(12) United States Patent
Mena Benito et al.

(10) Patent No.: US 10,925,548 B2
(45) Date of Patent: Feb. 23, 2021

(54) DEVICE, SYSTEM AND METHOD FOR DETECTION OF AN ASTHMA ATTACK OR ASTHMA OF A SUBJECT

(71) Applicant: KONINKLIJKE PHILIPS N.V., Eindhoven (NL)

(72) Inventors: Maria Estrella Mena Benito, Eindhoven (NL); Ihor Olehovych Kirenko, Veldhoven (NL); Ronaldus Maria Aarts, Geldrop (NL)

(73) Assignee: Koninklijke Philips N.V., Eindhoven (NL)

( * ) Notice: Subject to any disclaimer, the term of this patent is extended or adjusted under 35 U.S.C. 154(b) by 107 days.

(21) Appl. No.: 16/325,746

(22) PCT Filed: Aug. 17, 2017

(86) PCT No.: PCT/EP2017/070821
§ 371 (c)(1),
(2) Date: Feb. 15, 2019

(87) PCT Pub. No.: WO2018/036896
PCT Pub. Date: Mar. 1, 2018

(65) Prior Publication Data
US 2019/0200937 A1 Jul. 4, 2019

(30) Foreign Application Priority Data
Aug. 23, 2016 (EP) .................................... 16185302

(51) Int. Cl.
*A61B 5/00* (2006.01)
*A61B 5/113* (2006.01)
(Continued)

(52) U.S. Cl.
CPC .......... *A61B 5/7275* (2013.01); *A61B 5/0075* (2013.01); *A61B 5/0077* (2013.01);
(Continued)

(58) Field of Classification Search
CPC .... A61B 2560/0252; A61B 2562/0204; A61B 2562/0271; A61B 5/0075; A61B 5/0077;
(Continued)

(56) References Cited

U.S. PATENT DOCUMENTS 6,261,238 B1 7/2001 Gavriely
8,712,126 B2 * 4/2014 Piratla ................ G06K 9/00979
382/128
(Continued)

FOREIGN PATENT DOCUMENTS

WO WO2010015865 A1 2/2010
WO WO2011091268 A2 7/2011
(Continued)

OTHER PUBLICATIONS

Dixit et al., "Voice Parameter Analysis for the Disease Detection", IOSR Journal of Electronics and Communication Engineering (IOSR-JECE), vol. 9, No. 3, Jun. 2014, pp. 48-55, XP002767743.
(Continued)

*Primary Examiner* — Jonathan T Kuo
(74) *Attorney, Agent, or Firm* — Daniel H. Brean

(57) ABSTRACT

The present invention relates to a device (10, 10a, 10b), system (1, 2, 3) and method for detection of an asthma attack or asthma of a subject. For this purpose, the device comprises a light sensor input (11), e.g. a 2D camera, for obtaining light sensor data of the scene and a thermal sensor input (12), e.g. a thermal camera, for obtaining thermal sensor data of a scene including a subject while breathing. An analysis unit (13) obtains these data and derives respiratory effort information indicating respiratory efforts of the subject from the obtained light sensor data and/or the obtained thermal sensor data and derives airflow information indicating airflow during respiration of the subject from the obtained thermal sensor data. Further, the analysis unit (13)
(Continued)

predicts or detects an asthma attack or asthma based on analysis of the respiratory effort information and the airflow information, said analysis evaluating deviations from predetermined or healthy correlations between respiratory efforts and airflow.

20 Claims, 2 Drawing Sheets

(51) Int. Cl.
| | |
|---|---|
| A61B 5/087 | (2006.01) |
| A61B 5/01 | (2006.01) |
| G16H 50/20 | (2018.01) |
| G16H 30/40 | (2018.01) |
| G16H 50/30 | (2018.01) |
| A61B 5/0205 | (2006.01) |
| A61B 5/16 | (2006.01) |
| A61B 5/024 | (2006.01) |
| G16H 30/20 | (2018.01) |

(52) U.S. Cl.
CPC .............. *A61B 5/01* (2013.01); *A61B 5/015* (2013.01); *A61B 5/02055* (2013.01); *A61B 5/087* (2013.01); *A61B 5/1135* (2013.01); *A61B 5/165* (2013.01); *A61B 5/4803* (2013.01); *A61B 5/486* (2013.01); *A61B 5/4848* (2013.01); *A61B 5/7278* (2013.01); *G16H 30/20* (2018.01); *G16H 30/40* (2018.01); *G16H 50/20* (2018.01); *G16H 50/30* (2018.01); *A61B 5/02405* (2013.01); *A61B 5/0873* (2013.01); *A61B 2560/0252* (2013.01); *A61B 2562/0204* (2013.01); *A61B 2562/0271* (2013.01)

(58) Field of Classification Search
CPC ....... A61B 5/01; A61B 5/015; A61B 5/02055; A61B 5/02405; A61B 5/087; A61B 5/0873; A61B 5/1135; A61B 5/165; A61B 5/4803; A61B 5/4848; A61B 5/486; A61B 5/7275; A61B 5/7278; G16H 50/20; G16H 50/30; G06T 7/0012–7/0016; G06T 7/20–7/292; G06T 2207/30004–2207/30104; G06T 2207/30196–2207/30201
USPC ........................................................ 382/107
See application file for complete search history.

(56) References Cited

U.S. PATENT DOCUMENTS

| | | | | |
|---|---|---|---|---|
| 8,790,269 | B2* | 7/2014 | Xu | A61B 5/015 600/529 |
| 9,131,902 | B2 | 9/2015 | Halperin | |
| 9,301,710 | B2* | 4/2016 | Mestha | G06T 7/521 |
| 10,201,293 | B2* | 2/2019 | Bernal | A61B 5/0036 |
| 10,219,739 | B2* | 3/2019 | Mestha | A61B 5/7246 |
| 2006/0015263 | A1* | 1/2006 | Stupp | G06Q 50/22 702/19 |
| 2009/0012039 | A1* | 1/2009 | Kurtz | A61P 31/12 514/52 |
| 2012/0289850 | A1* | 11/2012 | Xu | A61B 5/015 600/529 |
| 2013/0236073 | A1* | 9/2013 | Piratla | G06K 9/00979 382/128 |
| 2013/0324875 | A1* | 12/2013 | Mestha | G06T 7/262 600/534 |
| 2014/0025396 | A1 | 1/2014 | Horseman | |
| 2014/0142456 | A1 | 5/2014 | Fischer | |
| 2014/0213925 | A1 | 7/2014 | Chan | |
| 2015/0094597 | A1* | 4/2015 | Mestha | A61B 5/1128 600/473 |
| 2015/0094606 | A1* | 4/2015 | Mestha | A61B 5/4818 600/534 |
| 2015/0265187 | A1* | 9/2015 | Bernal | A61B 5/4836 600/474 |
| 2016/0206216 | A1 | 7/2016 | Kirenko | |

FOREIGN PATENT DOCUMENTS

| | | | |
|---|---|---|---|
| WO | WO2014045257 | A1 | 3/2014 |
| WO | WO 2014198570 | A1 * | 12/2014 |
| WO | WO2015006364 | A2 | 1/2015 |
| WO | WO2015091302 | A1 | 6/2015 |

OTHER PUBLICATIONS

Khushb00 Batra, Swati Bhasin, Amandeep Singh: "Acoustic Analysis of Voice Samples to Differentiate Healthy and Asthmatic Persons", International Journal of Engineering and Computer Science, vol. 4, Jul. 7, 2015 (Jul. 7, 2015), pp. 13161-13164, XP002767744.
Murthy Javasimha N et al., "Thermal Infrared Imaging: a Novel Method to Monitor Airflow During Polysomnography.", Sleep, vol. 32, No. 11, Nov. 2009 (Nov. 2009), pp. 1521-1527.
Pereira Carina Barbosa et al: "Remote Monitoring of Breathing Dynamics Using Infrared Thermography" Biomedical Optics Express Nov. 1, 2015, vol. 6, No. 11, Nov. 1, 2015 (Nov. 1, 2015), pp. 4378-4394.
Fei J et al: "Analysis of Breathing Air Flow Patterns in Thermal Imaging", Conference Proceedings. Annual International Conference of the IEEE Engineering in Medicine and Biology Society (IEEE Cat. No. 06CH37748) IEEE Piscataway, NJ, USA, 2006, p. 946-952.
"Severe Eosinophilic Asthma—Identify & Diagnose Patients", The Free Dictionary by Farlex, Downloaded from the Internet Feb. 22, 2019, http://encyclopedia.thefreedictionary.com/asthma.
Severe Eosinophilic Asthma—Official Physician Website, The Free Dictionary by Farlex, Downloaded from the Internet Feb. 22, 2019, http://medical-dictionary.thefreedictionary.com/asthma.
"What Do You Want to Know About Asthma?", Healthline, by the Healthline Editorial Team and Kimberly Holland, Downloaded from the Internet Feb. 22, 2019, http://www.healthline.com/health/asthma.
Lehrer Paul M. et al., "Emotionally Triggered Asthma: A Review of Research Literature and Some Hypotheses for Self-Regulation Therapies", Applied Psychophysiology and Biofeedback, vol. 23, No. 1, pp. 13-41, Mar. 1998.
Chiang, Li-Chi et al., "Effect of Relaxation—Breathing Training on Anxiety and Asthma Signs/Symptoms of Children with Moderate to Severe Asthma: A Randomized Controlled Trial". International Journal of Nursing Studies, vol. 46, issue 8, pp. 1061-1071, Aug. 2009.
"AAFA: Asthma and allergy foundation of America", Downloaded from the Internet Feb. 22, 2019.
Gat A., "Asthma: Causes, Symptoms and Treatment News", Disabled World towards Tomorrow, updated Jun. 29, 2018 Downloaded form the Internet Mar. 12, 2019, http://www.disabled-world.com/artman/publish/asthma-attack.shtml.
"My Spiroo Can Use Your Smartphone to Predict Asthma Attacks", GeekTime, Apr. 20, 2014 Downloaded from the Internet Mar. 12, 2019, http://www.geektime.com/2014/04/20/my-spiroo-can-use-your-smartphone-to-predict-asthma-attacks/.
Bates C. et al., "Breath Test that Can Predict Asthma Attack the day Before they Happen", Daily Mail, Health Feb. 9, 2011, Downloaded from the Internet Mar. 12, 2019, http://www.dailymail.co.uk/health/article-1354903/Breath-sensor-predict-asthma-attack-day-strike.html.
Sandberg S. et al., "The Role of Acute and Chronic Stress in Asthma Attacks in Children", The Lancet, vol. 356, Issue 9234, Sep. 16, 2000, pp. 982-987.
Katon W.J. et al., "The Relationship of Asthma and Anxiety Disorders". Psychosomatic Medicine, vol. 66, pp. 349-355, 2004.

(56) References Cited

OTHER PUBLICATIONS

Devine E.C. et al., "Meta-Analysis of the Effects of Psychoeducational Care in Adults with Asthma", Research in Nursing & Health, vol. 19, pp. 367-376, 1996.

Lamontagne L.L. et al., "Effects of Relaxation on Anxiety in Children: Implications for Coping with Stress", Nursing Research, vol. 34, pp. 289-292, 1985.

Leher P.M. et al;, "Psychological Approaches to the Treatment of Asthma", Journal of Consulting and Clinical Psychology, vol. 60, Abstract Aug. 1992.

Thomas M. et al., "Breathing Exercises for Asthma", Breathe, vol. 10, Issue 4, pp. 312-322, Dec. 2014.

Chang Li-Chi et al., "Effect of Relaxation—Breathing Training on Anxiety and Asthma Signs/Symptoms of Children with Moderate to Severe Asthma: A Randomized Controlled Trial", International Journal of Nursing Studies, vol. 46, pp. 1061-1070, 2009.

\* cited by examiner

DEVICE, SYSTEM AND METHOD FOR DETECTION OF AN ASTHMA ATTACK OR ASTHMA OF A SUBJECT

CROSS-REFERENCE TO RELATED APPLICATIONS

This patent application claims the priority benefit under 35 U.S.C. § 371 of international patent application no. PCT/EP2017/070821, filed Aug. 17, 2017, which claims the benefit of European Patent Application No. 16185302.3, filed on Aug. 23, 2016, the contents of which are herein incorporated by reference.

FIELD OF THE INVENTION

The present invention relates to a device, system and method for detection of an asthma attack or asthma of a subject.

BACKGROUND OF THE INVENTION

Asthma is an inflammatory disease of the lungs. It makes breathing difficult and brings on attacks of coughing, wheezing, tightness in the chest and shortness of breath. According to the Centers for Disease Control and Prevention (CDC), approximately 25 million Americans suffer from asthma. It is the most common chronic condition among American children. About one in every 10 children has asthma.

Bronchial asthma is a multifactorial disease in which environmental, infectious, allergic, and psychological elements all play a part. This complex, multi-dimensional condition affects patients in many ways. Having asthma is inherently stressful and psychological problems are common and associated with poor asthma outcomes.

Although most patients in clinical trials can achieve high levels of control with optimized pharmacotherapy, in "real-life" practice, poor control is common, with over-reliance on rescue bronchodilator medication and ongoing symptoms and quality-of-life impairment. Asthma's increasing prevalence, severity and associated medical costs have triggered interest in new physiological and psychological intervention strategies including self-management, breathing-exercise techniques and mental relaxation.

An asthma attack can be terrifying for both children and adults. For people with asthma, having an "asthma management plan" is the best strategy to prevent an asthma attack. Effective self-management practices to control asthma symptoms and prevent flare-ups are known. These strategies include regular treatment with anti-inflammatory medication, regular medical review, and provision of support for people with asthma to self-regulate their asthma treatment and health related behaviors. Effective self-management practices include self-monitoring of asthma symptoms and/or lung function, medication adherence, and ownership of asthma action plans.

Prediction of an asthma attack is based on recognizing early warning signs, however sometimes it is not possible or reliable. Earlier, the only way to detect impending asthma attacks in advance was to conduct expensive pulmonary examinations. The best way to predict asthma attacks is to use a peak flow meter regularly and record the readings.

Many studies have focused just on physiological health even when an intervention has both physiological and psychological components. Stress and psychological factors have been shown by a growing body of evidence to trigger and exacerbate asthmatic conditions. Whatever precipitates an asthmatic attack, anxiety is likely to accompany it. For example, asthmatic children have been described as reacting to stressful situations and emotional distress in terms of anxiety, depression, and irritability. Furthermore, almost one-third of all children with asthma meet the criteria for comorbid anxiety disorders meaning that stress should be viewed as both a trigger and a consequence of this chronic disease. Relaxation training and relaxation techniques have been shown to make positive contributions to asthma management.

Asthma's increasing prevalence, severity and associated medical costs have triggered interest in new physiological and psychological intervention strategies including self-monitoring and self-management. Effective self-management practices include self-monitoring of asthma symptoms and/or lung function and ownership of asthma action plans. Self-monitoring of asthma is based on prediction and recognition of early warning signs. Unfortunately, sometimes it is not possible or reliable.

Asthma guidelines include pharmacotherapy strategy, but more and more physicians encourage the use of breathing-exercise techniques and mental relaxation for dealing with asthma. Many patients are interested in non-pharmacological treatments to improve asthma control, particularly breathing control exercises. A problem for many clinicians and patients is accessing therapists who can provide this training. Currently many patients who are interested in this type of treatment can only access it by paying unregulated therapists or by self-help books, internet pages or videos of unknown efficacy. Hence, there is a need for non-pharmacological approach to (self-) manage asthma and prevent serious asthma attacks.

U.S. Pat. No. 9,131,902 B2 discloses apparatus and methods for predicting an onset of a clinical episode. The apparatus includes a sensor, configured to sense at least one parameter of a subject substantially continuously during a period having a duration of at least one hour, and a control unit, configured to predict, at least one hour prior to the onset of the clinical episode, the onset at least in part responsively to the sensed parameter. Other applications are also described. The disclosed idea is based on using motion and other (non-camera) sensors for extraction of heart rate, respiration rate, motion and body temperature, performs an analysis of long term (at least one hour) pattern of heart rate, respiration rate, and compares it with the "normal" patterns to predict the offsets.

PEREIRA CARINA BARBOSA ET AL: "Remote monitoring of breathing dynamics using infrared thermography" BIOMEDICAL OPTICS EXPRESS 1 Nov. 2015, vol. 6, no. 11, 1 Nov. 2015, pages 4378-4394, ISSN: 2156-7085 discloses remote monitoring of breathing dynamics using infrared thermography. In particular, D1 presents a new robust algorithm to remotely monitor breathing rate by thermal imaging. This approach permits to detect and to track the region of interest as well as to estimate breathing rate.

FEI J ET AL: "Analysis of breathing air flow patterns in thermal imaging", CONFERENCE PROCEEDINGS. ANNUAL INTERNATIONAL CONFERENCE OF THE IEEE ENGINEERING IN MEDICINE AND BIOLOGY SOCIETY (IEEE CAT. NO. 06CH37748) IEEE PISCATAWAY, N.J., USA, 2006, page 7 pp, ISBN: 1-4244-0032-5 discloses a methodology to characterize breathing patterns based on thermal infrared imaging. The system disclosed is used to record the radiation information from within the breathing flow region. The method opens the way for desktop, unobtrusive monitoring of human respiration.

US 2016/206216 A1 discloses a device, system and method for skin detection. To enable a reliable, accurate and fast detection the proposed device comprises a thermal sensor input for obtaining thermal sensor data of a scene, a light sensor input for obtaining light sensor data of the scene, and an evaluation unit for analyzing the obtained thermal sensor data and the obtained light sensor data and for detecting skin areas within the scene based on said analysis.

SUMMARY OF THE INVENTION

It is an object of the present invention to provide a device, system and method for detection of an asthma attack or asthma of a subject allowing (self-) management of asthma and prevention of serious asthma attacks.

In a first aspect of the present invention a device for detection of an asthma attack or asthma of a subject is presented, said device comprising a light sensor input for obtaining light sensor data of the scene, said light sensor data comprising images in the visible and/or infrared light spectrum, a thermal sensor input for obtaining thermal sensor data of a scene including a subject while breathing, said thermal sensor data comprising thermal images in the longwave infrared spectrum, and an analysis unit for deriving respiratory effort information indicating respiratory efforts of the subject from the obtained light sensor data and for deriving airflow information indicating airflow during respiration of the subject from the obtained thermal sensor data and for predicting or detecting an asthma attack or asthma based on analysis of the respiratory effort information and the airflow information, said analysis evaluating deviations from predetermined or healthy correlations between respiratory efforts and airflow.

In a further aspect of the present invention a system for detection of an asthma attack or asthma of a subject is presented, said system comprising a light sensor for acquiring light sensor data of the scene, said light sensor data comprising images in the visible and/or infrared light spectrum, a thermal sensor for acquiring thermal sensor data of a scene, said thermal sensor data comprising thermal images in the longwave infrared spectrum, and a device as disclosed herein for detection of an asthma attack or asthma of a subject based on the acquired light sensor data and the acquired thermal sensor data.

In yet further aspects of the present invention, there are provided a corresponding method, a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, system, computer program and medium have similar and/or identical preferred embodiments as the claimed system, in particular as defined in the dependent claims and as disclosed herein.

The present invention is based on the idea to make use of the advantages of light sensor data (e.g. RGB camera data) and thermal sensor data (e.g. infrared camera data) to provide a reliable device, system and method for helping to recognize, control and manage asthma attacks and asthma in general. The sensor data may be acquired by a vital signs camera, as generally known in the field of remote photoplethysmography (rPPG) for unobtrusively and remotely acquiring vital signs of a subject. The advantages of such a vital signals camera can thus be combined with the effectiveness of a biofeedback-assisted personalized relaxation system. Those can be technologies that facilitate effective self-management practices (e.g. personal devices to self-monitor, platform systems for control asthma) and support patients to provide best practice asthma care.

With the present invention it may be possible to estimate the probability of developing an asthma attack and subsequently to provide biofeedback-assisted personalized treatment to the asthma patient. This could help to contribute to a personal way to manage asthma, and also to prevent serious asthma attacks that potentially require treatment in a hospital.

Camera-based monitoring of respiration and the acquisition of respiratory effort information indicating respiratory efforts of the subject can be provided in multiple ways. For instance, by using a thermal camera, breathing can be measured by monitoring changes of air temperature around nose or mouth. Moreover, by analyzing specific movements of a chest and/or a belly, breathing efforts can be measured, and the breathing rate can be extracted. By combining two sensor (e.g. camera) modalities (thermal and 2D motion), the combined analysis of the effort and airflow (indicating efficiency) of breathing can be achieved. These data can then be evaluated to reliably predict or detect an asthma attack or asthma.

Compared to the apparatus and methods disclosed in U.S. Pat. No. 9,131,902 B2, the device, system and method according to the present invention uses a different sensor (preferably camera) modalities (contrary to contact sensors) for remotely monitoring of several pieces of information simultaneously. Further, deviations, in particular instantaneous deviations, from predetermined or healthy correlations between an airflow (detected from the thermal sensor data) and respiratory efforts (detected by the light sensor data; optionally in addition by the thermal sensor data) may be identified to detect mismatches for predicting or detecting an asthma attack or asthma, i.e. no long term patterns of respiration rate are required.

In another embodiment said analysis unit is configured to evaluate, in the obtained light sensor data, motion of a body part, in particular the chest and/or belly portion, of the subject caused by respiration to derive the respiratory effort information. This provides an efficient way of obtaining the respiratory effort information, e.g. from camera data as light sensor data.

The analysis unit may further be configured to estimate a stress level of the subject from the obtained light sensor data and/or the obtained thermal sensor data and to take the estimated stress level into account in predicting or detecting an asthma attack or asthma. For instance, one or more vital signs, in particular heart rate and/or heart rate variability, of the subject may be determined from the obtained light sensor data and/or the obtained thermal sensor data to estimate a stress level of the subject. This information may also be used to check whether stress (e.g. detected from heart rate variability) is the reason for an asthma attack.

The device may further comprise an audio input for obtaining speech data of the subject representing speech of the subject, wherein said analysis unit is configured to estimate a stress level and/or derive respiratory information of the subject from the obtained speech data and to take the estimated stress level and/or the derived respiratory information into account in predicting or detecting an asthma attack or asthma. Thus, the efforts of the subject to speak loudly may be observed and evaluated.

The audio input may be configured to obtain speech data representing speech of the subject reading a text, in particular a predetermined text, wherein said analysis unit may be configured to derive reading information indicating reading difficulties and to take the derived reading information into account in predicting or detecting an asthma attack or asthma. If a person is not able to speak more than short phrases due to shortness of breath, or respiratory rate is increased significantly, that would indicate the beginning of the asthma attack. The severity of the attack can be evaluated objectively by analyzing the amount of breathing efforts, and/or the complexity of the text on which the person starts to experience problems with reading loudly.

Further, in an embodiment said analysis unit may be configured to derive air temperature change information indicating air temperature changes around mouth and/or nose of the subject from the obtained thermal sensor data and to take the derived air temperature change information into account in predicting or detecting an asthma attack or asthma. By measuring air temperature changes around mouth and nose breathing information can be easily obtained from the thermal sensor data.

The device may further comprise an output unit for issuing feedback information indicating feedback about a result of the detection and/or guidance information indicating guidance about actions to be performed to the subject. This supports self-management, treatment and/or prevention of an asthma attack.

Still further, the device may further comprise a data input for obtaining environmental data indicating the environment of the subject and/or medication data indicating medication, in particular allergens, administered to the subject, wherein said analysis unit is configured to take the obtained environmental data and/or the obtained medication data into account in predicting or detecting an asthma attack or asthma. This may particularly help to understand if an asthma event may be caused by a certain reason or if there is no real asthma event, but e.g. an allergic reaction caused by a medication or an environmental situation.

As explained above, the proposed system comprises a thermal sensor and a light sensor. The thermal sensor may comprise a longwave camera unit for acquiring thermal images in the longwave infrared spectrum. The light sensor may comprise an imaging unit for acquiring images in the visible and/or infrared light spectrum. The system may further comprise one or more of a microphone for generating speech data representing the speech of the subject, an environmental sensor for generating environmental data indicating the environment of the subject and/or a medication unit for generating medication data indicating medication, in particular allergens, administered to the subject.

According to an aspect of the present invention a method for enabling detection of an asthma attack or asthma of a subject is presented, said method comprising:

obtaining light sensor data of the scene, said light sensor data comprising images in the visible and/or infrared light spectrum, obtaining thermal sensor data of a scene including a subject while breathing, said thermal sensor data comprising thermal images in the longwave infrared spectrum, deriving respiratory effort information indicating respiratory efforts of the subject from the obtained light sensor data, deriving airflow information indicating airflow during respiration of the subject from the obtained thermal sensor data, and analyzing the respiratory effort information and the airflow information by evaluating deviations from predetermined or healthy correlations between respiratory efforts and airflow allowing to predict or detect an asthma attack or asthma based on said analysis.

The result of the evaluation of the deviations enables a practitioner, e.g. a doctor, to predict or detect an asthma attack or asthma. In an embodiment of the method the result of the evaluation of the deviations may additionally be used to automatically predict or detect an asthma attack or asthma.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
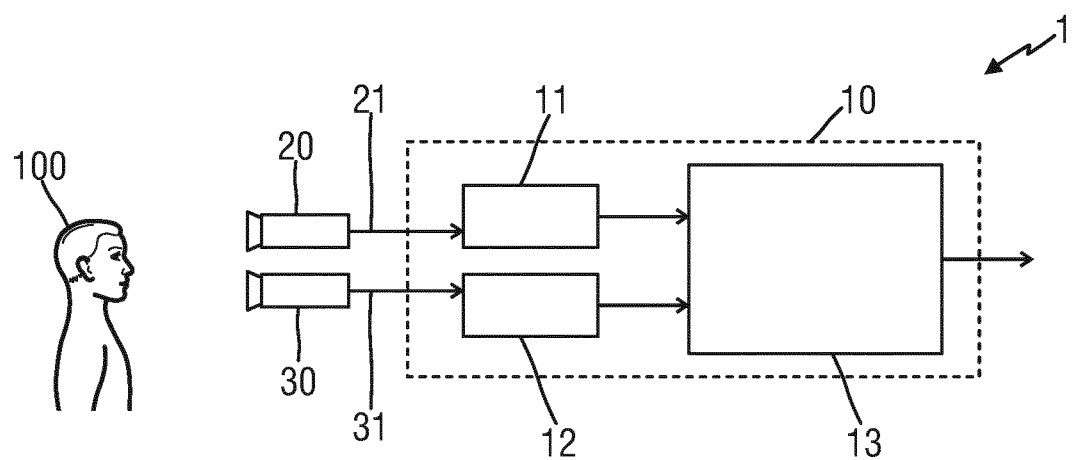
FIG. 1 shows a schematic diagram of a first embodiment of a device and a system according to the present invention.

FIG. 1 shows a schematic diagram of a first embodiment of a device 10 and a system 1 according to the present invention. According to this embodiment the system 1 comprises a light sensor 20, e.g. a video camera (such as an RGB camera), for acquiring light sensor data 21 of the scene, a thermal sensor 30, e.g. an infrared camera, for acquiring thermal sensor data 31 of a scene, and a device 10 detection of an asthma attack or asthma of a subject based on the acquired light sensor data 21 and the acquired thermal sensor data 31. The device 10 comprises a light sensor input 11, e.g. a wireless or wired interface for connection with the light sensor 20, for obtaining the light sensor data 21 of the scene and a thermal sensor input 12, e.g. a wireless or wired interface for connection with the thermal sensor 30, for obtaining the thermal sensor data 31 of the scene including a subject while breathing. The device 10 further comprises an analysis unit 13, e.g. a processor, for deriving respiratory effort information indicating respiratory efforts of the subject from the obtained light sensor data and/or the obtained thermal sensor data and for deriving airflow information indicating airflow during respiration of the subject from the obtained thermal sensor data and for predicting or detecting an asthma attack or asthma based on analysis of the respiratory effort information and the airflow information.

The device 10 and the corresponding method may be implemented in hard- and/or software, e.g. on a computer or processor loaded with corresponding software (e.g. an application (app')). For instance, a user device comprising a processor, such as a smartphone, tablet, laptop, PC, glasses, goggles (like a Google Glass-type of device) or wristwatch, may implement the device so that the user directly obtains the result of the detection, e.g. as feedback on the screen of the user device. In other embodiments the device 10 may be implemented as dedicated device specifically configured for the purpose of detecting an asthma attack or asthma of a subject.

In a practical implementation, the thermal sensor 30 comprises a longwave camera unit for acquiring thermal images in the longwave infrared spectrum and the light sensor 20 comprises an imaging unit, such as an RGB camera or an IR camera, for acquiring images in the visible and/or infrared (IR) light spectrum. If such a camera (or a vital signs camera as used in the field of remote photoplethysmography (rPPG)) is used as light sensor 20, various vital signs may be remotely acquired by use of the commonly known technique of rPPG, such as respiration rate, breathing patterns and (optionally) heart rate, which may be used separately or which may be evaluated by the analysis unit 13.

Figure 2:
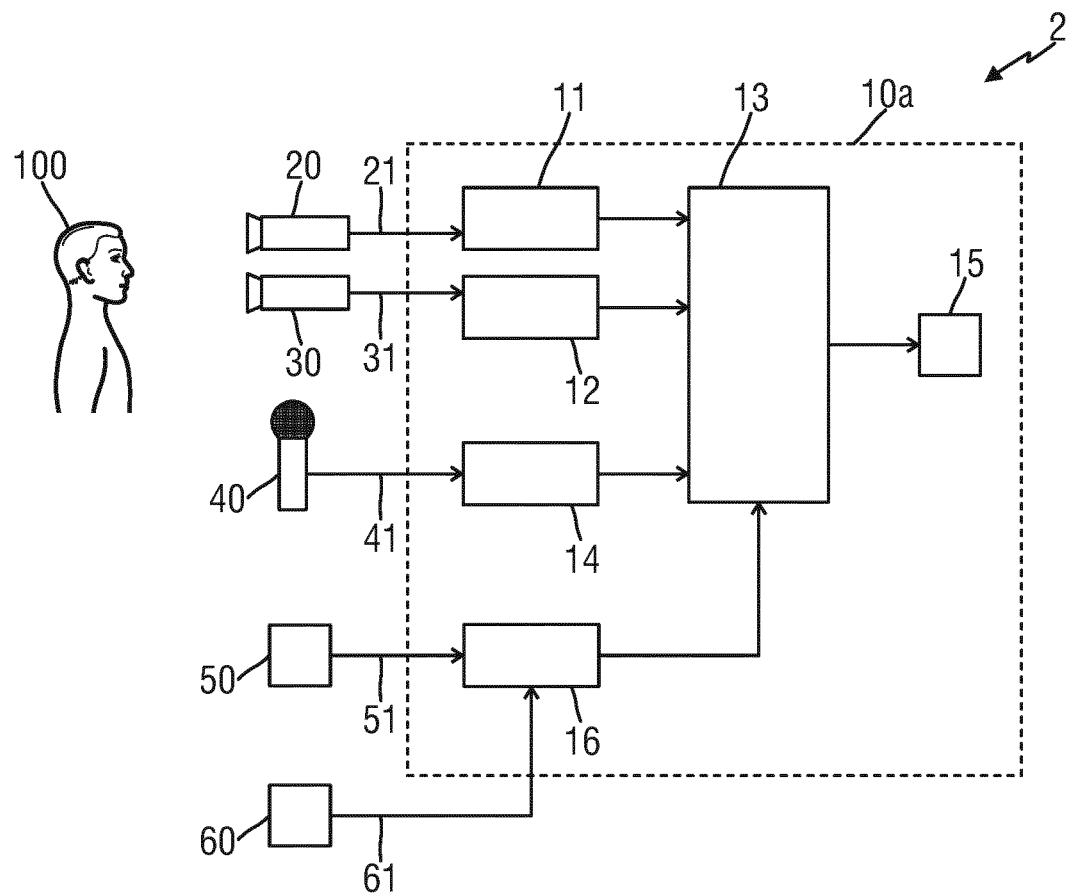
FIG. 2 shows a schematic diagram of a second embodiment of a device and a system according to the present invention.

FIG. 2 shows a schematic diagram of a second embodiment of a device 10a and a system 2 according to the present invention. In this embodiment the system 2 further a microphone 40 for generating speech data 41 representing the speech of the subject 100. The device 10a comprises a corresponding audio input 14 for obtaining said speech data and providing them to the analysis unit 13, where the speech data are additionally used for predicting asthma or an asthma attack.

In an embodiment, a stress level is estimated and/or respiratory information of the subject is derived from the obtained speech data 41 and the estimated stress level and/or the derived respiratory information is taken into account in predicting or detecting an asthma attack or asthma.

In another embodiment the speech data 41 represent speech of the subject 100 reading a text, in particular a predetermined text. The analysis unit 13 may then derive reading information indicating reading difficulties and to take the derived reading information into account in predicting or detecting an asthma attack or asthma.

The microphone 40 can further record breathing signals, detect coughs and wheezing, which information may additionally be evaluated by the analysis to further improve the prediction of asthma or asthma attacks.

The proposed device, system and method enable an evaluation of the possibility of developing asthma attack or estimate the severity of the attack. In an embodiment the subject 100 may be asked to undergo a set of tests, which involves breathing according to various breathing pattern and reading a certain text. For the first part of the test, a person is asked to follow respiratory patterns with various depths, frequency and type (chest vs. abdomen) of breathing. During this test, 2D and thermal camera-based monitoring is performed to analyze the correlation between the respiratory effort that a person has to take and the efficiency of breathing (amount of airflow) detected by a thermal camera. In the second part of the test, the person is asked to read loudly the sentences with increasing complexity. Meanwhile, the camera unit (including the 2D camera, as an embodiment of the light sensor 20) and/or the thermal camera (as an embodiment of the thermal sensor 30) and an audio microphone 40 monitor the efforts a person has to put to read loudly the complex text. If a person is not able to speak more than short phrases due to shortness of breath, or respiratory rate is increased significantly, that would indicate the beginning of the asthma attack. The severity of the attack can be evaluated objectively by analyzing the amount of breathing efforts and/or the complexity of the text on which the patient starts to experience problems with reading loudly.

All data is collected by the device (which may e.g. be configured as a smartphone, tablet, laptop, glasses, goggles (like a Google Glass-type of device), etc., in general as a user device), and may additionally be issued via an output unit 15, as shown in FIG. 2 as part of the device 10a, as feedback information indicating feedback about a result of the detection. Further, guidance information indicating guidance about actions to be performed to the subject 100 may be issued via the output unit 15. The output unit 15 may, for instance, be configured as user interface, e.g. as display or touchscreen. In another embodiment, the output unit 15 may be configured as transmission unit, e.g. for wireless (or wired) data transmission, preferably in real time, for instance using a WiFi network, a communication network, Bluetooth, Zigbee, or any other data transmission technique, to another entity, such as the subject's PC, a caregiver's PC or handheld device, a hospital workstation or archive, etc. For instance, the device 10a can be connected to an electronic health record of a hospital and may be able to send relevant information to a doctor, such as an asthma specialist at the hospital. This information can help to provide a more correct and feasibility diagnosis. This can be especially beneficial for those patients living in regional, rural and remote areas.

The complete multimodal system may thus be regarded as a biofeedback-assisted personalized relaxation system. The biofeedback-assisted personalized relaxation system may comprise a guided breathing exercise to reduce the stress level (as a possible source of the asthma attack) and the sensors to collect the information on the changes in respiratory effort, respiratory flow, and optionally Heart Rate Variability (HRV) measured by camera-based methods. Further, the collected information may be analyzed to monitor whether the personalized relaxation exercise makes a positive impact and whether stress was a major source of the asthma attack.

In a further embodiment, as also shown in FIG. 2, an environmental sensor 50 for generating environmental data 51 indicating the environment of the subject and/or a medication unit 60 for generating medication data 61 indicating medication, in particular allergens, administered to the subject may be provided. Accordingly, the device 10a further comprises a data input 16 for obtaining the environmental data 51 and/or the medication data 61.

The environmental data 51 may e.g. include data about the surrounding of the subject, such as air pollution, pollen, etc. The environmental sensor 50 could thus include a sensor that collects such environmental data, such as an air pollution sensor, pollen sensor, etc.

The device 10a is thus able to monitor the environmental situation of the asthma patient and consequently estimating the probability that triggers can activate asthma attack and therefore helping to avoid asthma attack.

The medication data 61 may e.g. include information about the kind, dose, timing, etc. of medication, in particular allergens, administered to the subject, which may have an influence on the subject's health, i.e. which particularly contribute to causing asthma or an asthma attack or which may be the source of the subject's condition looking like an asthma attack but being in fact a different reaction, e.g. an allergic reaction of the subject 100 in response to a certain medication. The medication unit 60 could thus be a unit where information about the medication is entered by a user or a medication dispenser which automatically registers dispensed medication. The device 10a can thus improve the reliability by monitoring the amount of e.g. allergen materials applied and therefore helping to avoid inappropriate or incorrect diagnosis for the individual patient, but also a much more feasible way in the comparison of patch test results.

The analysis unit 13 is thus preferably configured to take the obtained environmental data 51 and/or the obtained medication data 61 into account in predicting or detecting an asthma attack or asthma.

Figure 3:
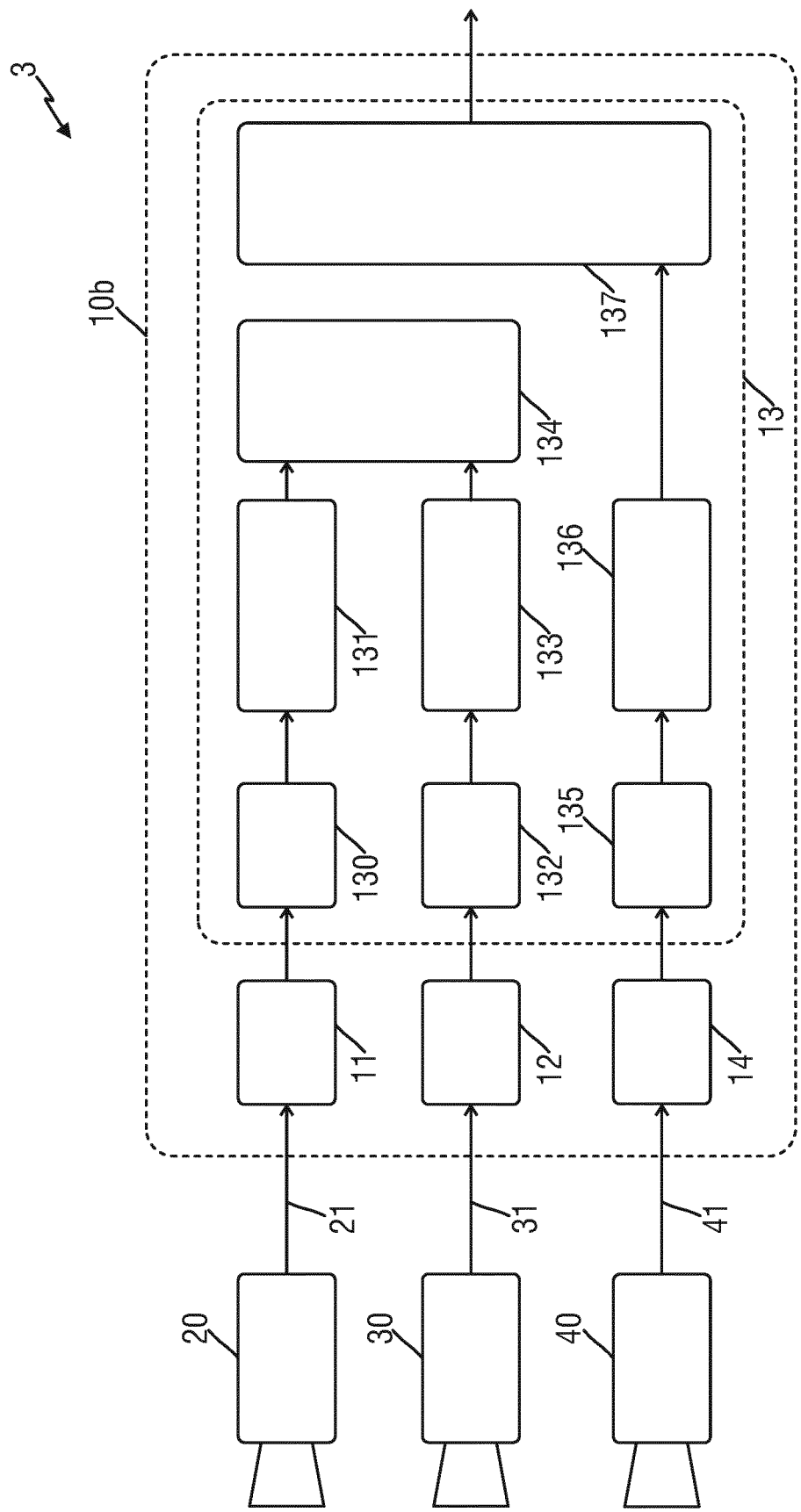
FIG. 3 shows a schematic diagram of a third embodiment of a device and a system according to the present invention.

FIG. 3 shows a schematic diagram of a third embodiment of a device 10b and a system 3 according to the present invention. FIG. 3 shows particularly more details of an embodiment of the processing chain for the prediction of the asthma attack and evaluation of its severity.

This embodiment of the proposed system 3 comprises three main elements:

Registration of the breathing pattern condition on normal state: objective baseline estimation and comparison of breathing pattern to the registered baseline.

Real-time guidance on evolution: personalized bio-feedback.

Spot-check or continuous monitoring of breathing rate during onset.

The system 3 comprises at least a set of cameras 20, 30 or a camera unit integrating these cameras 20, 30 for 2D and thermal image acquisition and an audio microphone 40, the data of which are used for predicting the probability of having an asthma attack and for estimating its severity.

The analysis unit 13 can evaluate when an asthma suffer is close to have an asthma attack by combined analysis of heat flow during breathing and respiratory effort. For this purpose the analysis unit 13, in this embodiment, comprises a motion analysis unit 130 for analyzing motion in the light sensor data 21 (in this case 2D image data) and respiratory effort estimation unit 131 for estimating the respiratory effort from the analyzed motion. From the 2D image data it is further possible to analyze the subject's breathing pattern (chest or belly breathing), respiratory rate, respiratory effort and the air flow, which information may also be evaluated for the final prediction and detection.

A heat flow analysis unit 132 is provided for analyzing heat flow from the thermal sensor data 31 and an air flow estimation unit 133 for estimating the respiratory air flow from the analyzed heat flow. In a breathing efficiency analysis unit 134 the estimated respiratory effort and the estimated air flow are analyzed to obtain information on the breathing efficiency.

Moreover, the analysis unit 13 comprises a voice analysis unit 135 for analyzing the speech data 41 of the subject, e.g. to detect the disruption of a speech during a stimulus (e.g. reading a complex text loudly). Further, a stress level estimation unit 136 is provided for estimating the stress level of the subject during the stimulus based on the analysis of the speech data.

A prediction unit 137 is provided for detecting or predicting asthma or an asthma attack and/or for estimating the severity/level of an asthma attack based on the result of the prior analyses.

In an embodiment a display may be provided, as an output unit 15 (as shown in FIG. 2) to show the breathing patterns, which should be followed by a subject during a personalized relaxation exercise.

The proposed way of analysis automatically performed by the device has the advantages of being much easier to use for asthma patients compared to the actual ways to predict asthma attacks. The optionally provided relaxation exercise helps to normalize the breathing patterns to a monitored base line. On the basis of this deviation, the device can decide if the relaxation exercise needs to be activated. Further on, the device can finalize the relaxation exercise when it estimates that the breathing rate is controlled and consequently the asthma episode is over. Additionally, the proposed device can provide help to adopt a slower respiratory rate with longer expiration and reduction in overall ventilation. This can be done at the onset of and/or during asthma attacks.

The present invention thus provides a self-monitoring system, device and method having several advantages, including allowing patients to analyze their breath themselves and also helping to be less anxious of having an asthma attack. The device, system and method according to the present invention are aimed to be used for self-monitoring, control and management of asthma attacks and asthma in general. Further, they can be used for people suffering for hyperventilation or for those experience breathing problems, i.e. while suffering from influenza.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for detection of an asthma attack or asthma of a subject, said device comprising:
   a light sensor input for obtaining light sensor data, produced via alight sensor, of a scene that includes the subject, wherein said light sensor data comprises images in a visible and/or an infrared light spectrum,
   a thermal sensor input for obtaining thermal sensor data, produced via a thermal sensor, of the scene that includes the subject while breathing, wherein said thermal sensor data comprises thermal images in a longwave infrared spectrum, and
   an analysis unit for (i) deriving respiratory effort information by evaluating in the obtained light sensor data motion of a body part of the subject caused by respiration, (ii) deriving air temperature change information indicating air temperature changes at least partially caused by respiration of the subject from the obtained thermal sensor data, and (iii) predicting information and the air temperature change information, wherein said analysis comprises evaluating deviations of the derived respiratory effort information and derived air temperature change information from predetermined or healthy correlations between respiratory efforts and air temperature changes, the analysis unit further for generating output data indicative of the predicted or detected asthma attack or asthma.

2. The device as claimed in claim 1, wherein the analysis unit is further configured to derive respiratory effort information by evaluating in the obtained light sensor data and the obtained thermal sensor data motion of the body part of the subject caused by respiration.

3. The device as claimed in claim 1, wherein said analysis unit is configured to evaluate, in the obtained light sensor data, motion of a chest and/or belly portion of the subject caused by respiration to derive the respiratory effort information.

4. The device as claimed in claim 1, wherein said analysis unit is further configured to estimate a stress level of the subject from the obtained light sensor data and/or the obtained thermal sensor data, and to predict or detect the asthma attack or asthma further based on the estimated stress level.

5. The device as claimed in claim 4, wherein said analysis unit is further configured to determine one or more vital signs of the subject from the obtained light sensor data and/or the obtained thermal sensor data to estimate the stress level of the subject.

6. The device as claimed in claim 5, wherein the one or more vital signs comprise heart rate and/or heart rate variability.

7. The device as claimed in claim 1, further comprising an audio input for obtaining speech data, produced via a microphone, of the subject representing speech of the subject, wherein said analysis unit is further configured to estimate a stress level and/or derive respiratory information of the subject further from the obtained speech data, and to predict or detect the asthma attack or asthma further based on the estimated stress level and/or the further derived respiratory information.

8. The device as claimed in claim 7, wherein said audio input is configured to obtain speech data, produced via the microphone, representing speech of the subject reading a text, and wherein said analysis unit is further configured to derive reading information indicating reading difficulties encountered by the subject in reading the text, and to predict or detect the asthma attack or asthma further based on the derived reading information.

9. The device as claimed in claim 1, wherein said analysis unit is configured to further derive air temperature change information indicating air temperature changes around mouth and/or nose of the subject from the obtained thermal sensor data and to predict or detect the asthma attack or asthma further based on the further derived air temperature change information.

10. The device as claimed in claim 1, further comprising an output unit, responsive to the generated output data, for issuing feedback information indicating feedback about a result of the detection and/or guidance information indicating guidance about actions to be performed.

11. The device as claimed in claim 1, further comprising a data input for obtaining (i) environmental data, produced via an environmental sensor, indicating a characteristic of an environment of the subject and/or (ii) medication data, produced via a medication unit, indicating medication administered to the subject, wherein said analysis unit is configured to predict or detect the asthma attack or asthma further based on the obtained environmental data and/or the obtained medication data.

12. The device as claimed in claim 11, wherein the medication comprises allergens.

13. A system for detection of an asthma attack or asthma of subject, said system comprising:
    a light sensor for acquiring light sensor data of a scene, wherein said light sensor data comprises images in a visible and/or infrared light spectrum,
    a thermal sensor for acquiring thermal sensor data of the scene, wherein said thermal sensor data comprises thermal images in the longwave infrared spectrum, and
    a device as claimed in claim 1 for detection of the asthma attack or asthma of a subject based on the acquired light sensor data and the acquired thermal sensor data.

14. The system as claimed in claim 13, wherein said thermal sensor comprises a longwave camera unit for acquiring said thermal images in the longwave infrared spectrum and/or said light sensor comprises an imaging unit for acquiring said images in the visible and/or infrared light spectrum.

15. The system as claimed in claim 13, further comprising one or more of a microphone for generating speech data representing speech of the subject, an environmental sensor for generating environmental data indicating the environment of the subject and/or a medication unit for generating medication data indicating medication administered to the subject.

16. The system as claimed in claim 15, wherein the medication comprises allergens.

17. A method for enabling detection of an asthma attack or asthma of a subject, said method comprising:
    obtaining, via a light sensor, light sensor data of a scene, wherein said light sensor data comprises images in a visible and/or an infrared light spectrum,
    obtaining, via a thermal sensor, thermal sensor data of the scene that includes the subject while breathing, wherein said thermal sensor data comprises thermal images in alongwave infrared spectrum,
    deriving, via an analysis unit, respiratory effort information by evaluating in the obtained light sensor data motion of a body part of the subject caused by respiration,
    deriving, via the analysis unit, air temperature change information indicating air temperature changes at least partially caused by respiration of the subject form the obtained thermal sensor data, and
    analyzing, via the analysis unit, the respiratory effort information and the air temperature change information by evaluating deviations of the derived respiratory effort information and derived air temperature change information from predetermined or healthy correlations between respiratory efforts and air temperature changes to predict or detect the asthma attack or asthma based on said analysis, and further generating, via the analysis unit, output data indicative of the predicted or detected asthma attack or asthma.

18. The method as claimed in claim 17, wherein deriving respiratory effort information further comprises by evaluating in the obtained light sensor data and the obtained thermal sensor data motion of the body part of the subject caused by respiration.

19. The method as claimed in claim 17, further comprising:
    estimating, via the analysis unit, a stress level of the subject from the obtained light sensor data and/or the obtained thermal sensor data, and to predict or detect the asthma attack or asthma further based on the estimated stress level.

20. The method as claimed in claim 17, further comprising:
    obtaining speech data, via a microphone, of the subject representing speech of the subject, wherein analyzing, via the analysis unit, further comprises estimating a stress level and/or deriving respiratory information of the subject further from the obtained speech data, and to predict or detect the asthma attack or asthma further based on the estimated stress level and/or the further derived respiratory information.

* * * * *